(12) United States Patent
Price et al.

(10) Patent No.: US 7,319,733 B2
(45) Date of Patent: Jan. 15, 2008

(54) SYSTEM AND METHOD FOR IMAGING USING MONOENERGETIC X-RAY SOURCES

(75) Inventors: John Scott Price, Niskayuna, NY (US); William Robert Ross, Scotia, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/951,132

(22) Filed: Sep. 27, 2004

(65) Prior Publication Data

US 2006/0067460 A1  Mar. 30, 2006

(51) Int. Cl.
*G01N 23/00* (2006.01)

(52) U.S. Cl. ............................................. 378/5; 378/62

(58) Field of Classification Search ................ 378/143, 378/168, 169, 185, 184, 4–20, 62, 86–90
See application file for complete search history.

(56) References Cited

U.S. PATENT DOCUMENTS

| | | | |
|---|---|---|---|
| 4,260,885 A * | 4/1981 | Albert | 378/45 |
| 5,416,815 A * | 5/1995 | Hsieh | 378/4 |
| 6,546,075 B1 | 4/2003 | Chartier et al. | 378/98 |
| 6,687,333 B2 * | 2/2004 | Carroll et al. | 378/119 |
| 7,027,553 B2 * | 4/2006 | Dunham et al. | 378/5 |
| 2003/0016789 A1 | 1/2003 | Harding et al. | 378/143 |
| 2004/0066894 A1 | 4/2004 | Holz et al. | 378/84 |
| 2004/0101088 A1 | 5/2004 | Sabol et al. | 378/4 |
| 2004/0101104 A1 | 5/2004 | Avinash et al. | 378/98.12 |
| 2004/0208286 A1 * | 10/2004 | Richardson | 378/119 |

* cited by examiner

*Primary Examiner*—Hoon Song
(74) *Attorney, Agent, or Firm*—Fletcher Yoder

(57) ABSTRACT

An imaging system is provided for various non-invasive medical and non-medical imaging. The imaging system includes a tunable X-ray source for emitting X-rays having a substantially monoenergetic spectrum and an energy discriminating detector for generating a detector output signal in response to the X-rays incident on the energy discriminating detector. The imaging system also includes a system controller comprising an X-ray controller for operating the tunable X-ray source and data acquisition circuitry for acquiring the detector output signal from the energy discriminating detector.

27 Claims, 4 Drawing Sheets

SYSTEM AND METHOD FOR IMAGING USING MONOENERGETIC X-RAY SOURCES

BACKGROUND

The invention relates generally to X-ray imaging and in particular to X-ray imaging using monoenergetic X-ray sources and energy discriminating detectors.

X-rays have found widespread application in various non-invasive medical and non-medical imaging techniques. In general, X-ray based imaging systems direct an X-ray beam toward an object to be imaged. The X-ray beam may be generated by an X-ray tube or by other techniques. In conventional X-ray imaging systems, the generated X-rays typically have a broad spectrum that may be representative of the technique and/or materials used to generate the X-rays. The generated X-rays typically pass through an imaging volume containing an object or patient. As the X-rays pass through the object or patient, the different materials of which the object or patient are composed attenuate the X-rays to varying degrees. For example, bone, metal, water, air, and soft tissue attenuate the X-rays differently. As attenuated X-rays leave the imaging volume they typically strike a detector where they generate electrical signals that are processed to generate an image of the internal structures of the object or patient.

The X-rays produced in common X-ray tubes are generally of relatively low power, and comprise long pulses or a continuous wave that pose limitations in their use. Moreover, such radiation typically comprises unpolarized, incoherent radiation having a broad energy spectrum. In general, the X-rays generated by conventional techniques may be useful for imaging techniques where the attenuation is measured to produce images, but they are less useful in techniques where energy-dependent information of the materials under inspection are also of interest.

For example, X-ray attenuation through a given object is not constant and is strongly dependent on the X-ray photon energy. This phenomenon manifests itself in an image as a beam-hardening artifact, such as non-uniformity, shading and streaks. Some beam-hardening artifacts can be easily corrected by techniques such as water calibration and iterative bone correction. However, beam hardening from materials other than water and bone, such as metals and contrast agents, are difficult to correct. In addition, the same materials at different locations often show different levels of attenuation. Another limitation of conventional imaging system is lack of material characterization. For example, a highly attenuating material with a low density may result in the same degree of attenuation in the image as a less attenuating material with a high density. Thus, there is little or no information about the material composition of a scanned object based solely on the degree of attenuation. In addition, visibility of certain contrast agents in the human body may be enhanced by imaging the body with properly selected portions of the X-ray spectrum.

Traditional techniques for producing monoenergetic X-ray beams such as fluorescent sources and Bragg angle scattered X-rays for energy selection are employed for various medical applications to overcome the above mentioned limitation. Filtration of a broadband bremsstrahlung radiation can also produce spectra of desired monochromaticity. For example, in mammography, rhodium-coated targets coupled with thin rhodium filtration produces relatively narrow portions of X-ray spectrum centered around the energy of interest. However, in certain cases a significant portion of the X-rays have energies too low to penetrate far into the human body, thereby failing to contribute to an image of the region of interest. In short, a wide X-ray photon energy spectrum from the X-ray source and a lack of energy resolution from the X-ray detectors limit the use of imaging systems for applications such as material characterization, tissue differentiation, scatter rejection and others.

It is therefore desirable to provide an efficient imaging system having monoenergetic X-ray source and energy discriminating detectors to achieve better image contrast and high resolution while minimizing the image noise and radiation doses to the patient.

BRIEF DESCRIPTION

Briefly in accordance with one aspect of the technique, an imaging system is provided. The imaging system includes a tunable X-ray source configured to emit X-rays having a substantially monoenergetic spectrum and an energy discriminating detector configured to generate a detector output signal in response to the X-rays incident on the energy discriminating detector. The imaging system also includes a system controller comprising an X-ray controller configured to operate the tunable X-ray source and data acquisition circuitry configured to acquire the detector output signal from the energy discriminating detector.

In accordance with another aspect of the technique, an imaging system is provided. The imaging system includes an X-ray source configured to emit X-rays having a substantially monoenergetic spectrum and an energy discriminating detector configured to generate a detector output signal in response to the X-rays incident on the energy discriminating detector. The imaging system also includes a system controller comprising an X-ray controller configured to operate the X-ray source and data acquisition circuitry configured to acquire the detector output signal from the energy discriminating detector. In addition, the imaging system includes image reconstruction circuitry configured to generate at least one composition image based on the detector output signal.

In accordance with a further aspect of the present technique, a method is provided for generating a composition image. The method provides for selecting a desired monoenergetic X-ray spectrum for imaging an object of interest, emitting X-rays generally at the desired monoenergetic X-ray spectrum through the object of interest, detecting the X-rays attenuated by the object of interest via an energy discriminating detector, generating a detector output signal in response to the X-rays detected by the energy discriminating detector and generating at least one composition image based on the detector output signal. Systems and computer programs that afford functionality of the type defined by this method may be provided by the present technique.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques are generally directed to X-ray imaging using monoenergetic X-rays and energy discriminating detectors. Such imaging techniques may be useful in a variety of imaging contexts, such as CT imaging, industrial inspection systems, CT metrology, X-ray radiography, non-destructive testing, heavy metals analysis, security and baggage screening, and others. Though the present discussion provides examples in a medical imaging context, one of ordinary skill in the art will readily apprehend that the application of these techniques in other contexts, such as for industrial imaging, security screening, and/or baggage or package inspection, is well within the scope of the present techniques.

Figure 1:
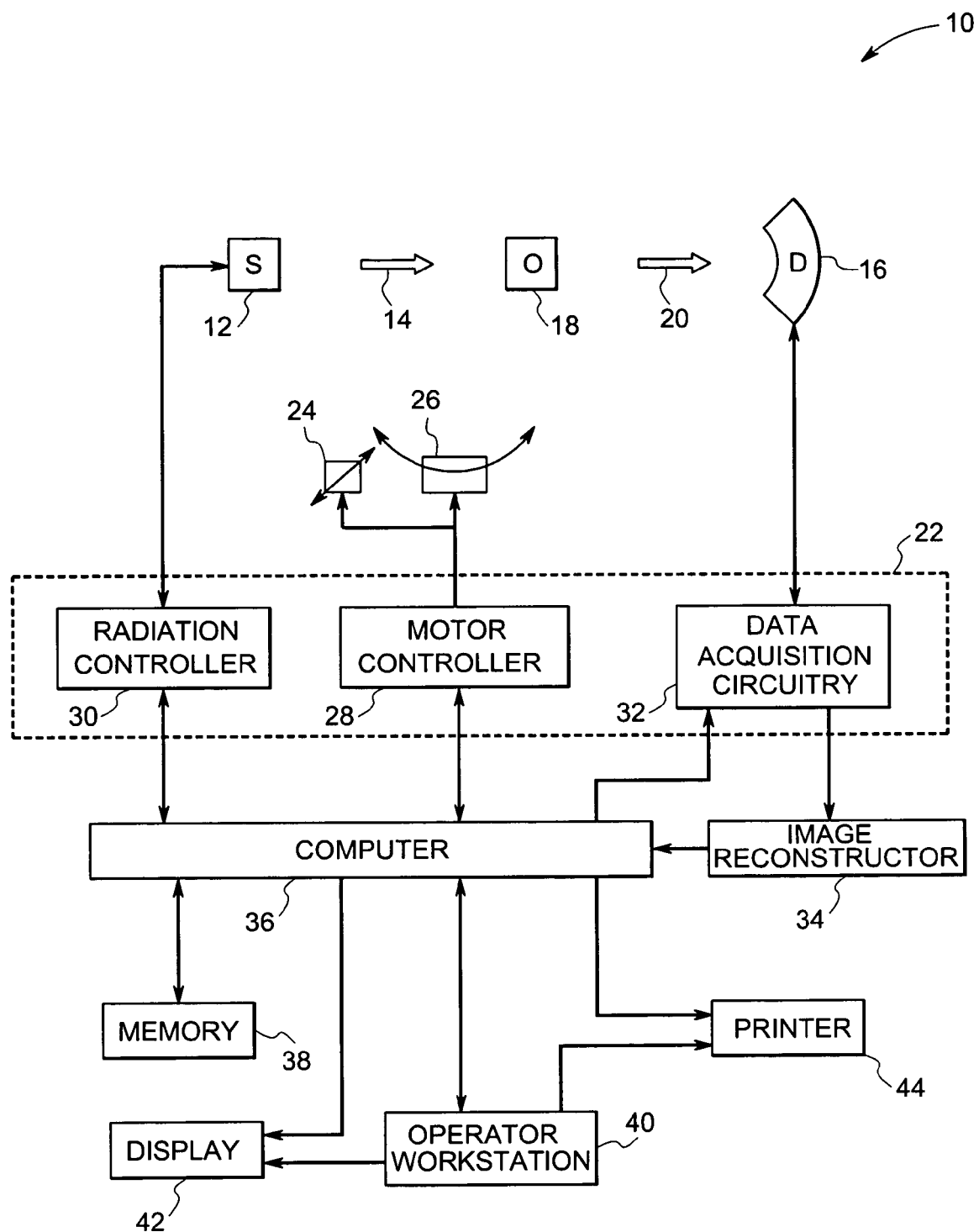
FIG. 1 depicts an exemplary imaging system using a monoenergetic X-ray source and energy sensitive detectors in accordance with one aspect of the present technique.

Referring now to FIG. 1, an imaging system 10 for use in accordance with the present technique is illustrated. In the illustrated embodiment, the imaging system 10 includes a radiation source 12, such as an X-ray source. A collimator may be positioned adjacent to the radiation source 12 for regulating the size and shape of a stream of radiation 14 that emerges from the radiation source 12. The imaging system 10, as well as other imaging systems based on X-ray attenuation, may employ X-ray sources that generate X-rays by a variety of techniques. For example, the present technique employs a tunable X-ray source that may be configured to emit monoenergetic or nearly monoenergetic X-rays at one or more energy levels.

Figure 4:
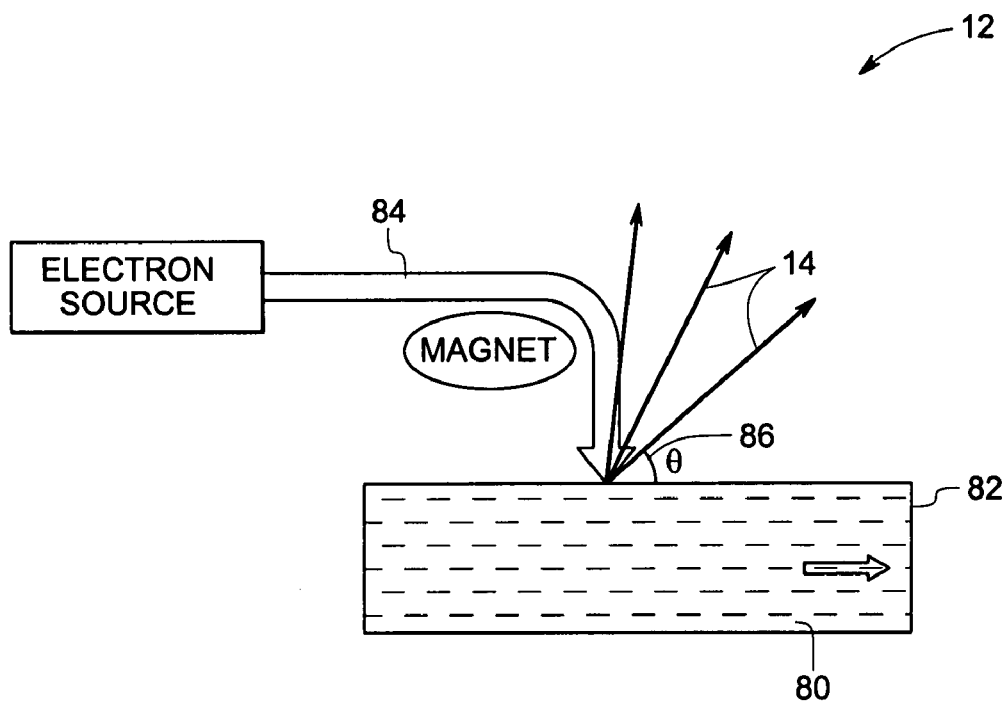
FIG. 4 depicts an X-ray source employing a liquid metal target for use in the imaging system of FIG. 1.
Figure 5:
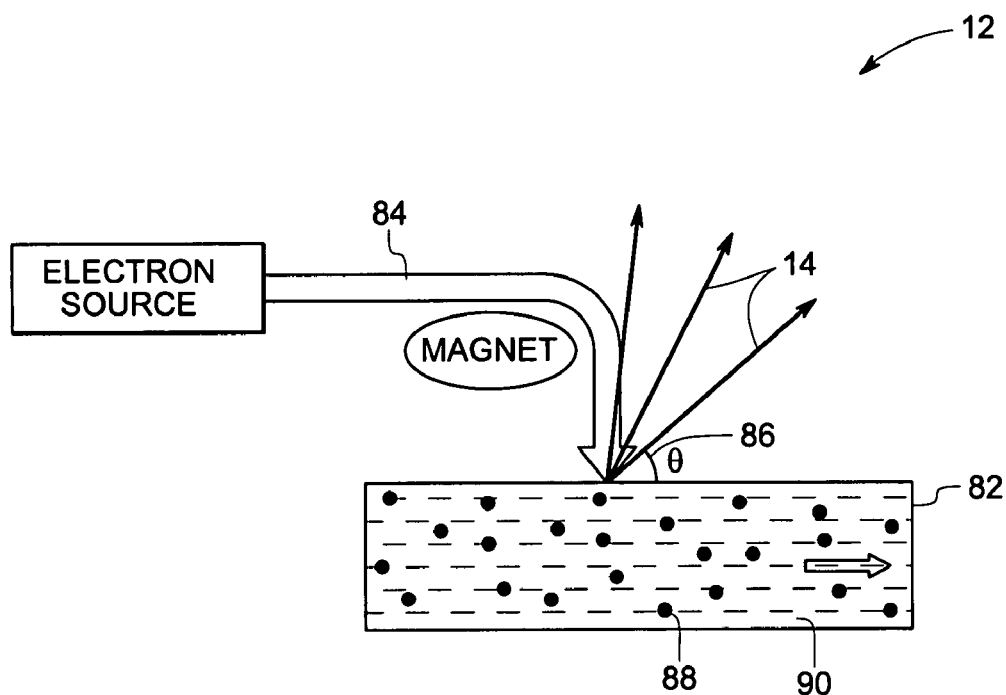
FIG. 5 depicts an X-ray source employing metal particles suspended in liquid medium as target for use in the imaging system of FIG. 1.

A variety of techniques may be employed to generate the monoenergetic or nearly monoenergetic X-rays at a desired spectrum. Such techniques include but are not limited to inverse Compton scattering processes, plasma based X-ray emission, and filtration of a broadband bremsstrahlung radiation. For example, in one embodiment, the monoenergetic X-rays 14 are generated at a desired spectrum by an X-ray tube 12 having a liquid metal target 80, as illustrated in FIG. 4. A liquid metal or liquid metal suspension carrier flows through a conduit 82 to form the target for an 80 keV to 200 keV electron beam 84. The electron beam 84 creates X-rays 14 by impact with a thin cross-section of the flowing target 80. Different target materials result in different spectra of X-rays. The selection of a desired characteristic X-ray spectrum and suppression of broadband bremsstrahlung radiation by filtering and proper choice of exit angle 86 makes the source nearly monoenergetic. In one embodiment, one or more solid particles 88 of various metals, crystals, and/or other solid materials may be suspended in the liquid carrier 90, as illustrated in FIG. 5. Suspension of target particles 88 in the liquid carrier 90 allows choice of targets and spectra as well as efficient heat dissipation for relatively high average power operation. Further, the target particles 88 enable selection of wavelength for a monochromatic or quasi-monochromatic source.

In typical operation, the radiation source 12 projects a stream of radiation 14, such as a monoenergetic X-ray beam, towards a detector array 16 placed on the opposite side of the radiation source 12. The stream of radiation 14 passes into an imaging volume in which an object 18 to be imaged may be positioned. It should be noted that a particular region of the object 18 may be chosen by an operator for imaging so that the most useful scan of the region may be acquired.

A portion of the radiation 20 passes through or around the object and impacts the detector array 16. The detector array 16 may be a single slice detector or a multi-slice detector and is generally formed as an array of detection elements. Each detector element produces an electrical signal that represents the intensity of the incident radiation 20 at the detector element when the radiation 20 strikes the detector array 16. These signals are acquired and processed to reconstruct an image of the features internal as well external to the object 18.

In one implementation, the detector array may be an energy discriminating detector designed to distinguish between different portions of X-ray spectra or different X-ray energy levels. There are different methods to obtain multi-energy measurements using energy sensitive detectors. For example, in one implementation energy sensitive detectors may be employed such that each X-ray incident on the detector is recorded with its energy.

It should be noted that a wide variety of energy discriminating detectors may be used to detect and resolve the attenuated X-rays of different energy levels. Such energy discriminating detectors include, but are not limited to, charge integrating detectors, photon counting detectors and other energy sensitive detectors. Further, these detectors may directly convert the X-rays to electrical signals for processing. Alternatively, these detectors may use a scintillating material to convert X-rays to optical radiation that may be detected and converted to electrical signals for processing. Also, a wide variety of energy sensitive detectors such as semiconductor detectors and arrays, high density noble gas detectors, phosphors, scintillators, thin film transistor arrays, charge coupled devices, microchannel plates and calorimetric detectors may be employed for energy discrimination.

Referring back to FIG. 1, the object 18 and the radiation source 12 are typically displaced relative to each other, allowing projection data to be acquired at various views relative to the object 18 if desired. For example, the object 18 may be positioned on a table, such as a turntable, so that the object 18 may be rotated during the examination process to expose all sides of the object 18 to the stream of radiation 14. Alternatively, the radiation source 12 and/or the detector array 16 may be disposed on a gantry, which may be rotated around the object 18 during the examination process. As the object 18 and the radiation source 12 rotate relative to each other, the detector array 16 collects data of radiation attenuation at the various view angles relative to the object 18. Data collected from the detector array 16 then undergoes pre-processing and calibration to condition the data to represent the line integrals of the attenuation coefficients of the scanned objects 18. The processed data, commonly called projections, are then reconstructed to formulate one or more composition images of the scanned area, as discussed in greater detail below. Thus, an image or slice is acquired which may incorporate, in certain modes, less or more than 360 degrees of projection data, to formulate an image.

Operation of the source 12 is controlled by a system controller 22, which furnishes both power, and control signals for examination sequences. Moreover, the detector array 16 is coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, system controller 22 commands operation of the imaging system 10 to execute examination protocols and to process acquired data. In the present context, system controller 22 may also include signal processing circuitry and other circuitry, typically based upon a general purpose or application-specific digital computer, associated memory circuitry for storing programs and routines executed by the computer, as well as configuration parameters and image data, interface circuits, and so forth. Indeed, the system controller 22 may be implemented as hardware and software components of the depicted computer 36.

In the embodiment illustrated in FIG. 1, the system controller 22 is coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated one or multiple turns around the object 18. It should be noted that the rotational subsystem 26 might include a gantry. Thus, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 enables the object 18 to be displaced linearly, such as by moving a table or support on which the object 18 rests. Thus, in one embodiment, the table may be linearly moved within a gantry to generate images of particular areas of the object 18.

Additionally, as will be appreciated by those skilled in the art, the radiation source 12 may be controlled by a radiation controller 30 disposed within the system controller 22. Particularly, the radiation controller 30 may be configured to provide power and timing signals to the radiation source 12. In one embodiment, the monoenergetic spectrum of X-ray emission is user selectable and the X-ray source may be tuned via the radiation controller 30 to emit X-rays at or near the selected spectrum, thereby making the X-ray source tunable.

Further, the system controller 22 may include data acquisition circuitry 32. In this exemplary embodiment, the detector array 16 is coupled to the system controller 22, and more particularly to the data acquisition circuitry 32. The data acquisition circuitry 32 typically receives sampled analog signals, representative of the location and energy of the incident monoenergetic X-rays, from the detector array 16 and converts the data to digital signals for subsequent processing. An image reconstructor 34, that is coupled to or is a part of a computer 36, may receive sampled and digitized data from the data acquisition circuitry 32 and may perform high-speed image reconstruction to generate one or more composition image of the scanned object 18. Alternatively, reconstruction of the image may be done by general or special purpose circuitry of the computer 36. Once reconstructed, the image produced by the imaging system 10 reveals internal as well as external features of the object 18.

The computer 36 may include or be in communication with a memory 38. It should be understood that any type of memory to store a large amount of data may be utilized by such an exemplary imaging system 10. In addition, the computer 36 may be configured to receive commands and scanning parameters from an operator via an operator workstation 40. For example, the operator workstation 40 may be equipped with a keyboard and/or other input devices by which an operator may control the imaging system 10. Thus, the operator may observe the reconstructed image and other data relevant to the system from computer 36, initiate imaging, select a spectrum for imaging and so forth. It should be noted that the spectrum is selected based upon the type of imaging requirement such as soft tissue imaging, bone imaging, contrast imaging, radiography of a particular metal and/or other imaging requirements.

A display 42 may be coupled to one of the operator workstation 40 and the computer 36 and may be utilized to observe the one or more composition image and/or to control imaging. Additionally, the scanned image may also be printed by a printer 44 which may be coupled to the computer 36 and/or the operator workstation 40, either directly or over a network. It should be further noted that the computer 36 and/or operator workstation 40 may be coupled to other output devices that may include standard or special purpose computer monitors and associated processing circuitry. Furthermore, additional operator workstations may be further linked in the imaging system 10 for outputting system parameters, requesting inspection, viewing images, selecting an X-ray spectrum for imaging and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

Figure 2:
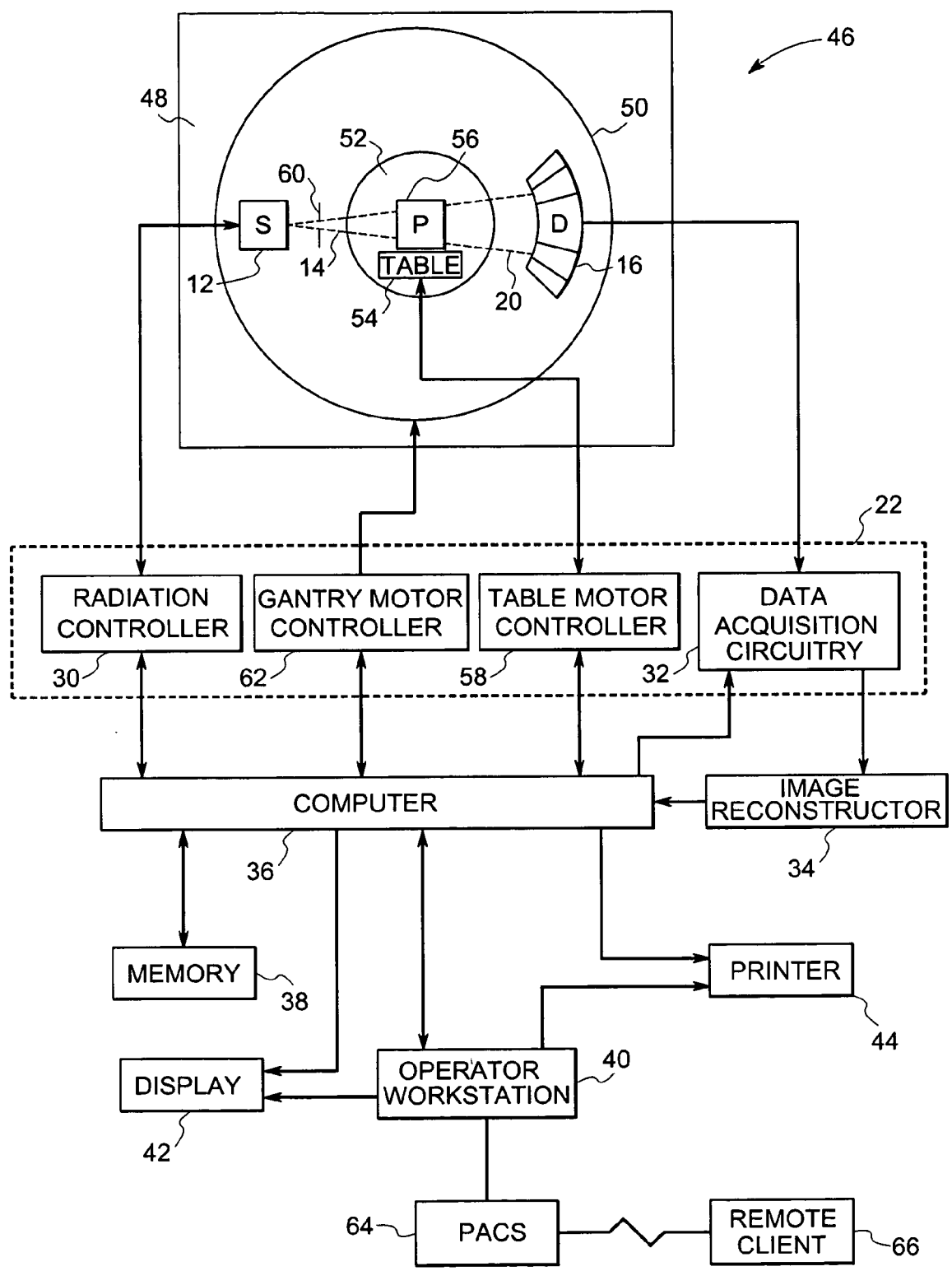
FIG. 2 depicts an exemplary CT imaging system for volumetric imaging using a monoenergetic X-ray source and energy sensitive detectors in accordance with one aspect of the present technique.

Referring generally to FIG. 2, an exemplary medical imaging system utilized in a present embodiment may be a computed tomography (CT) system designed both to acquire original image data for and to process the image data for display and analysis in accordance with the present technique. The CT imaging system 46 is an energy discriminating computed tomography system as the detector subsystem is designed to record the individual photon energies of different monoenergetic X-ray spectra. The CT imaging system 46 is illustrated with a frame 48 and a gantry 50 that has an aperture (imaging volume or CT bore volume) 52. A patient table 54 is positioned in the aperture 52 of the frame 48 and the gantry 50. The patient table 54 is adapted so that a patient 56 may recline comfortably during the examination process. Additionally, the table 54 is configured to be displaced linearly by the linear positioning subsystem 24 (see FIG. 1) as discussed above. For example, in the illustrated embodiment, a table motor controller 58 that may be a part of the system controller 22 may be adapted to operate the table 54.

The gantry 50 includes an X-ray source 12 positioned adjacent to a collimator 60. In typical operation, the X-ray source 12 projects monoenergetic X-rays at one or more specified energy levels towards the energy discriminating detector 16 mounted on the opposite side of the gantry 50. Collimator 60 permits a stream of radiation 14 to pass into a particular region in which a subject, such as a human patient 56 is positioned. It should be noted that the particular region of the patient 56, for instance the liver, pancreas and so on, is typically chosen by an operator so that the most useful scan of a region may be acquired.

Furthermore, the gantry 50 may be rotated around the subject 56 so that a plurality of radiographic views may be collected along an imaging trajectory described by the motion of the X-ray source 12 relative to the patient 56. In particular, as the X-ray source 12 and the detector array 16 rotate along with the CT gantry 50, the detector array 16 collects data of X-ray beam attenuation at the various view angles relative to the patient 56. As described above, these data may then be processed to generate one or more composition image of the scanned area of the patient 56.

Rotation of the gantry 50 and operation of the source 12 is controlled by a system controller 22 as discussed above. As described above, the rotational subsystem 26 (see FIG. 1) is configured to operate the gantry 50. For example, in the illustrated embodiment, the system controller 22 may include a gantry motor controller 62 that controls the rotational speed and position of the gantry 50. The computer 36 is typically used to control the entire CT system 46 and may be adapted to control features enabled by the system controller 22. The computer 36 in turn may be configured to receive commands and scanning parameters from an operator via an operator workstation 40.

In the illustrated embodiment, the operator workstation 40 may also be coupled to a picture archiving and communications system (PACS) 64. It should be noted that PACS 64 may be coupled to a remote system 66, such as radiology department information system (RIS), hospital information system (HIS) or to an internal or external network, so that others at different locations may gain access to the image and to the image data.

While in the present discussion reference is made to a CT scanning system in which a source and detector rotate on a gantry arrangement, it should be borne in mind that the present technique is not limited to data collected on any particular type of scanner. For example, the technique may be applied to data collected via a scanner in which an X-ray source and a detector are effectively stationary and an object is rotated, or in which the detector is stationary but an X-ray source rotates or otherwise moves relative to the detector or imaged object. Further, the data could originate in a scanner in which both the X-ray source and detector are stationary, as where the X-ray source is distributed and can generate X-rays at different locations. Similarly, while generally circular scan geometries are discussed, other geometries may be envisioned as well.

Figure 3:
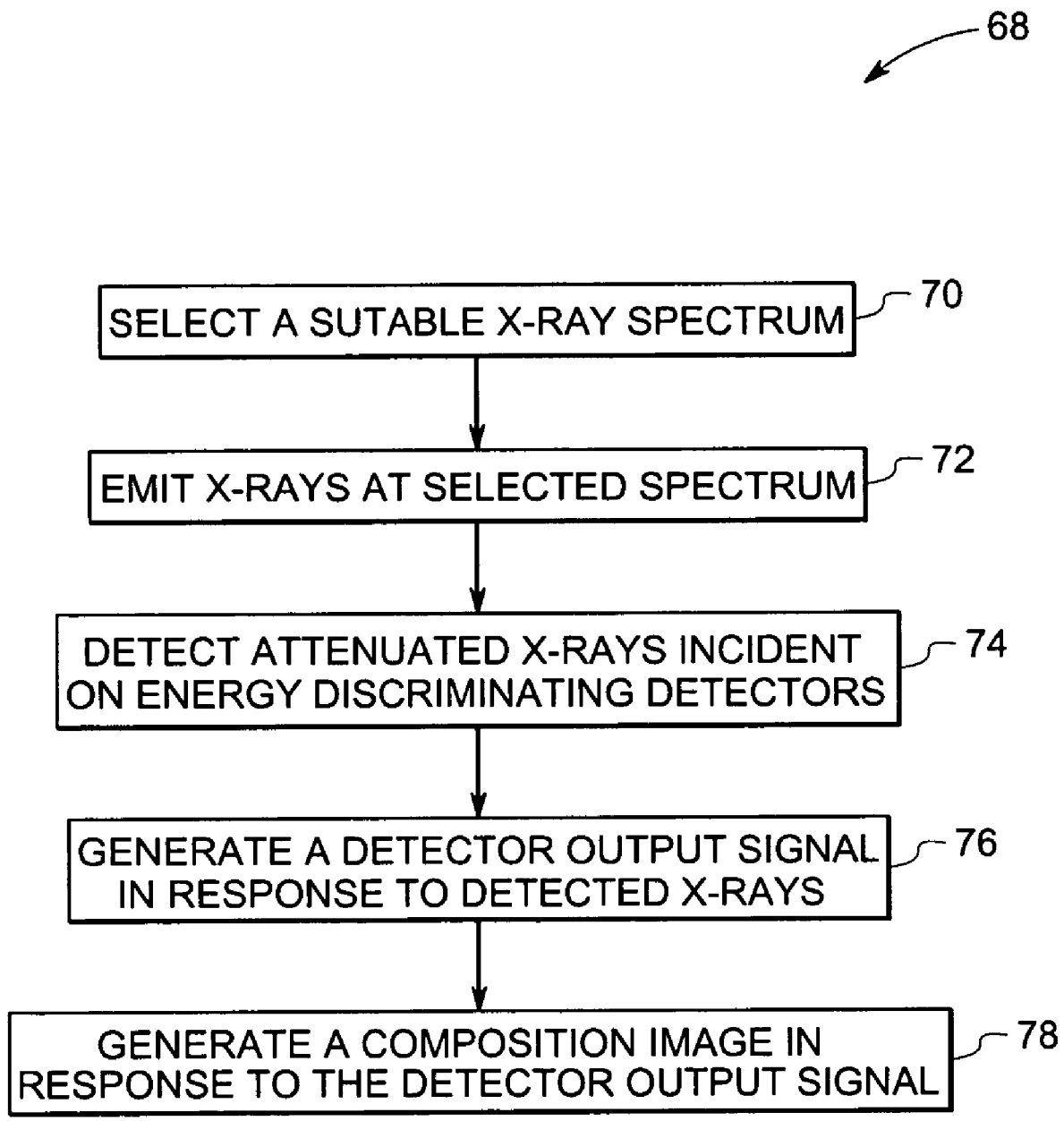
FIG. 3 is a flowchart illustrating method of generating composition image in accordance with one aspect of the present technique.

The imaging system 10 and the CT imaging system 46 may generate images of the object under examination by a variety of techniques. For example, referring now to FIG. 3, exemplary control logic for generating one or more composition image using a monoenergetic X-ray source and an energy discriminating detector is depicted. As illustrated in the flowchart 68, an operator may select a desired monoenergetic X-ray spectrum for imaging an object of interest at step 70. The desired monoenergetic X-ray spectrum may be selected based on the type of imaging being performed such as contrast imaging, bone imaging, soft tissue imaging, material characterization and others. The X-rays are then emitted at the desired monoenergetic spectrum via a tunable monoenergetic X-ray source through the object of interest at step 72. Alternatively, the X-rays may be emitted at a broader spectrum than desired and be filtered so that they are essentially monoenergetic when they reach the imaging volume.

Further, the monoenergetic X-rays are attenuated by the object of interest and detected by the energy discriminating detector at step 74 that generates a detector output signal in response to the detected X-rays at step 76. Each detector output signal contains spectral information about the composition of the scanned image based on the degree of attenuation of the monoenergetic X-rays in the scanned image. The detector output signal is therefore processed by an image processing circuitry to generate one or more composition image of the scanned object at step 78.

The imaging system 10 as described in the various embodiments discussed above, provides better diagnostic ability via better tissue differentiation, higher contrast per unit dose to the patient, better scatter rejection and better image quality. Since the X-rays are monoenergetic, selective elements of the object under scrutiny can be emphasized. In one embodiment, the present technique enables the rejection of scattered X-rays (referred to as scatter in the art) due to the ability to discriminate the energy of detected photons. The limited spectrum enables mitigation of energy-dependent differential attenuation effects which otherwise lead to beam hardening. Reduced beam hardening and scatter reduces computed tomography artifacts, thereby improving tissue differentiation and diagnostic power. In addition, the ability to tune narrow band X-ray spectra enhances material differentiation.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system comprising:
   a tunable X-ray source configured to emit X-rays having a substantially monoenergetic spectrum, the tunable X-ray source comprising a target comprising a liquid metal or a plurality of one or more types of particles suspended in a liquid medium;
   an energy discriminating detector configured to generate a detector output signal in response to the X-rays incident on the energy discriminating detector; and
   a system controller comprising an X-ray controller configured to operate the tunable X-ray source and data acquisition circuitry configured to acquire the detector output signal from the energy discriminating detector.

2. The imaging system of claim 1, wherein the tunable X-ray source generates the X-rays via at least one of a plasma based X-rays emission technique or a technique comprising filtering of a broadband bremsstrahlung radiation.

3. The imaging system of claim 1, wherein the energy discriminating detector comprises at least one of charge integrating detectors, photon counting detectors or energy sensitive detectors.

4. The imaging system of claim 1, wherein the tunable X-ray source emits the X-rays at different locations relative to an imaging volume.

5. The imaging system of claim 1, further comprising image reconstruction circuitry configured to generate at least one composition image based on the detector output signal.

6. The imaging system of claim 5, further comprising an operator workstation configured to monitor the at least one composition image.

7. The imaging system of claim 1, wherein the tunable X-ray source is configured by an operator interface to emit X-rays generally at a desired monoenergetic spectrum.

8. The imaging system of claim 7, wherein the desired monoenergetic spectrum is selected to perform at least one of contrast imaging, bone imaging or soft tissue imaging.

9. An imaging system comprising:
   a tunable X-ray source configured to emit X-rays having a substantially monoenergetic spectrum, the X-ray source comprising a target comprising a liquid metal or a plurality of one or more types of particles suspended in a liquid medium;

an energy discriminating detector configured to generate a detector output signal in response to the X-rays incident on the energy discriminating detector;

a system controller comprising an X-ray controller configured to operate the X-ray source and data acquisition circuitry configured to acquire the detector output signal from the energy discriminating detector; and image reconstruction circuitry configured to generate at least one composition image based on the detector output signal.

10. The imaging system of claim 9, wherein the X-ray source generates the X-rays via at least one of a plasma based X-rays emission technique or a technique comprising filtering of a broadband bremsstrahlung radiation.

11. The imaging system of claim 9, wherein the energy discriminating detector comprises at least one of charge integrating detectors, photon counting detectors or energy sensitive detectors.

12. The imaging system of claim 9, wherein the X-ray source emits the X-rays at different locations relative to an imaging volume.

13. The imaging system of claim 12, further comprising an operator workstation configured to monitor the at least one composition image.

14. A method of generating a composition image, the method comprising:

selecting a desired monoenergetic X-ray spectrum for imaging an object of interest;

emitting X-rays generally at the desired monoenergetic X-ray spectrum through the object of interest via a tunable X-ray source, the tunable X-ray source comprising a target comprising a liquid metal or a plurality of one or more types of particles suspended in a liquid medium;

detecting the X-rays attenuated by the object of interest via an energy discriminating detector;

generating a detector output signal in response to the X-rays detected by the energy discriminating detector; and generating at least one composition image based on the detector output signal.

15. The method of claim 14, wherein emitting the X-rays comprises generating the X-rays via at least one of a plasma based X-rays emission technique or a technique comprising filtering of a broadband bremsstrahlung radiation.

16. The method of claim 14, wherein emitting the X-rays comprises emitting the X-rays at different locations relative to an imaging volume.

17. The method of claim 14, further comprising monitoring the at least one composition image via an operator workstation.

18. The method of claim 14, wherein selecting the desired monoenergetic X-ray spectrum comprises selecting the desired monoenergetic X-ray spectrum to perform at least one of contrast imaging, bone imaging or soft tissue imaging.

19. A computer readable media, comprising:

code adapted to trigger emission of X-rays generally at a desired monoenergetic X-ray spectrum through an object of interest via a tunable X-ray source, the tunable X-ray source comprising a target comprising a liquid metal or a plurality of one or more types of particles suspended in a liquid medium;

code adapted to detect the X-rays attenuated by the object of interest via an energy discriminating detector;

code adapted to generate a detector output signal in response to the X-rays detected by the energy discriminating detector; and code adapted to generate at least one composition image based on the detector output signal.

20. The computer readable media of claim 19, further comprising code adapted to monitor the at least one composition image via an operator workstation.

21. An imaging system comprising:

a tunable X-ray source configured to emit X-rays having a substantially monoenergetic spectrum via an inverse Compton scattering technique;

an energy discriminating detector configured to generate a detector output signal in response to the X-rays incident on the energy discriminating detector; and a system controller comprising an X-ray controller configured to operate the tunable X-ray source and data acquisition circuitry configured to acquire the detector output signal from the energy discriminating detector.

22. The imaging system of claim 21, wherein the energy discriminating detector comprises at least one of charge integrating detectors, photon counting detectors or energy sensitive detectors.

23. The imaging system of claim 21, further comprising image reconstruction circuitry configured to generate at least one composition image based on the detector output signal.

24. The imaging system of claim 21, wherein the tunable X-ray source is configured by an operator interface to emit X-rays generally at a desired monoenergetic spectrum.

25. The imaging system of claim 24, wherein the desired monoenergetic spectrum is selected to perform at least one of contrast imaging, bone imaging or soft tissue imaging.

26. A method of generating a composition image, the method comprising:

selecting a desired monoenergetic X-ray spectrum for imaging an object of interest;

emitting X-rays generally at the desired monoenergetic X-ray spectrum through the object of interest via an inverse Compton scattering technique;

detecting the X-rays attenuated by the object of interest via an energy discriminating detector;

generating a detector output signal in response to the X-rays detected by the energy discriminating detector; and generating at least one composition image based on the detector output signal.

27. The method of claim 26, wherein selecting the desired monoenergetic X-ray spectrum comprises selecting the desired monoenergetic X-ray spectrum to perform at least one of contrast imaging, bone imaging or soft tissue imaging.

* * * * *